United States Patent [19]

Hayashi et al.

[11] Patent Number: 5,214,197
[45] Date of Patent: May 25, 1993

[54] 2,4-DIHYDROXYADIPIC ACID DERIVATIVE

[75] Inventors: Shigeo Hayashi, Takasago; Noboru Ueyama; Kenji Inoue, both of Kakogawa; Teruyoshi Koga, Takasago; Satomi Takahashi, Kobe, all of Japan

[73] Assignee: Kanegafuchi Chemical Industry Co., Ltd., Osaka, Japan

[21] Appl. No.: 724,728

[22] Filed: Jul. 2, 1991

[30] Foreign Application Priority Data

Jul. 6, 1990 [JP] Japan .................................. 2-179874
Feb. 18, 1991 [JP] Japan .................................. 3-046076

[51] Int. Cl.$^5$ ............................................. C07C 69/66
[52] U.S. Cl. ..................................... 560/176; 560/180; 560/146; 560/186; 562/582; 562/578; 562/587; 549/449; 549/375; 556/437
[58] Field of Search ............... 560/180, 176, 146, 186; 562/582, 578, 587; 549/375; 556/437

[56] References Cited

FOREIGN PATENT DOCUMENTS 374922 6/1990 European Pat. Off. .

OTHER PUBLICATIONS

Suemune, H. et al., Tetrahedron Asymmetry vol. 1, No. 7, pp. 425–428 1990.
*Chemical Abstracts*, vol. 114, No. 5, Feb. 4, 1991, Abstract No. 42336s.

*Primary Examiner*—Paul J. Killos
*Attorney, Agent, or Firm*—Wegner, Cantor, Mueller & Player

[57] ABSTRACT

A novel 2,4-dihydroxyadipic acid derivative of the formula:

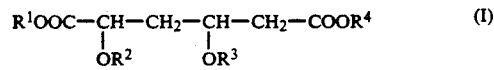

wherein $R^1$ and $R^4$ are the same or different and each a hydrogen atom, an alkyl group, an aralkyl group, an aryl group or a silyl group, and $R^2$ and $R^3$ are the same or different and each a hydrogen atom or a protective group of a hydroxy group or together form a ring, which is useful as a common intermediate in the synthesis of HMG-CoA reductase inhibitor.

20 Claims, No Drawings

2,4-DIHYDROXYADIPIC ACID DERIVATIVE

BACKGROUND OF THE INVENTION

1. Field of the Invention

The present invention relates to a 2,4-dihydroxyadipic acid derivative, a process for preparing the same and a process for converting the same to 3,5,6-trihydroxyhexanoic acid derivative.

The 2,4-dihydroxyadipic acid derivative is a novel compound which is useful as a common intermediate in the synthesis of a series of HMG-CoA (hydroxy methyl glutarylCoA) reductase inhibitors which are attractive as having a function of antihyperlipemia.

2. Description of the Related Art

Hitherto, no 2,4-dihydroxyadipic acid derivative has been synthesized, or there is no report on the use of the 2,4-dihydroxyadipic acid derivative in the production of the HMG-CoA reductase inhibitors. As an intermediate in the synthesis of the HMG-CoA reductase inhibitor, 3,5,6-trihydroxyhexanoic acid derivative has been mainly used. For the synthesis of the 3,5,6-trihydroxyhexanoic acid derivative, there are known a process comprising reacting an enolate of an acetate or its equivalent with a 3,4-dihydroxybutyric acid derivative to increase the number of carbon atoms and reducing the resulting 5,6-dihydroxyhexanoic acid derivative (cf. Japanese Patent Kokai Publication Nos. 22056/1988 and 199945/1989) and a process utilizing asymmetric epoxidation of allyl alcohol (cf. Tetrahedron Letters, 25, 3391 (1984)). For the synthesis of 3,5-dihydroxy-6-oxohexanonate derivative, there are known a process comprising oxidation of 3,5,6-trihydroxyhexanoate derivative (cf. Japanese Patent Kokai Publication No. 199945/1989) and a process comprising oxidation of a styrene derivative with ozone (cf. J. Med. Chem., 33, 2982 (1980)).

However, the above processes are not necessarily practical processes for the industrial production of 3,5,6-trihydroxyhexanoic acid derivative, since, for example, the process utilizing the 3,4-dihydroxybutyric acid derivative has a drawback that comparatively expensive reagents and complicated procedures are required for the protection and deprotection of the hydroxy groups, and the process utilizing the asymmetric epoxidation of allyl alcohol has a drawback that it is difficult to selectively obtain a (3R,5S) isomer having a high activity as the HMG-CoA reductase inhibitor.

SUMMARY OF THE INVENTION

An object of the present invention is to provide a novel 2,4-dihydroxyadipic acid derivative.

Another object of the present invention is to provide an intermediate in the production of a novel 2,4-dihydroxyadipic acid.

A further object of the present invention is to provide a process for preparing the novel 2,4-dihydroxyadipic acid derivative.

A yet further object of the present invention is to provide a process for converting the 2,4-dihydroxyadipic acid derivative to 3,5,6-trihydroxyhexanoic acid derivative.

According to a first aspect of the present invention, there is provided a 2,4-dihydroxyadipic acid derivative of the formula:

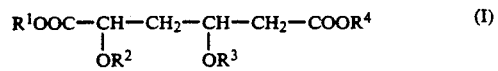

wherein $R^1$ and $R^4$ are the same or different and each a hydrogen atom, an alkyl group, an aralkyl group, an aryl group or a silyl group, and $R^2$ and $R^3$ are the same or different and each a hydrogen atom or a protective group of a hydroxy group or together form a ring.

According to a second aspect of the present invention, there is provided a 2-hydroxy-4-oxoadipic acid derivative of the formula:

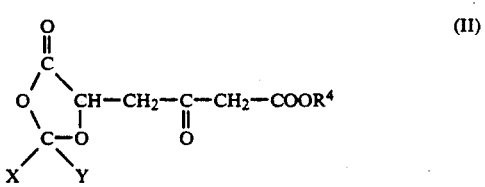

wherein $R^4$ is the same as defined above, and X and Y are the same or different and each a hydrogen atom, an alkyl group, an aralkyl group or an aryl group or together form a ring.

According to a third aspect of the present invention, there is provided a 2-hydroxy-4-oxoadipic acid derivative of the formula:

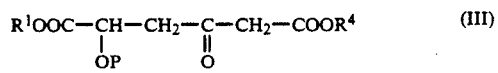

wherein $R^1$ and $R^4$ are the same as defined above, and P is an hydrogen atom or a protective group of a hydroxy group.

According to a fourth aspect of the present invention, there is provided a 2,4-dihydroxyadipic acid derivative of the formula:

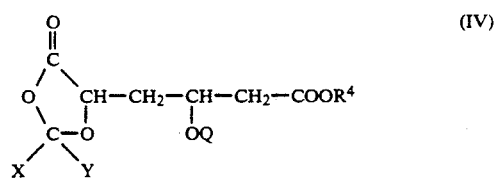

wherein X, Y and $R^4$ are the same as defined above, and Q is a hydrogen atom or a protective group of a hydroxy group.

According to a fifth aspect of the present invention, there is provided a process for preparing the 2,4-dihydroxyadipic acid derivative (I) comprising reacting the 2-hydroxy-4-oxoadipic acid derivative (II) with a metal alkoxide to obtain the 2-hydroxy-4-oxoadipic acid derivative (III), reducing the 2-hydroxy-4-oxoadipic acid derivative (III) and optionally deprotecting the hydroxy group and/or hydrolyzing the ester group.

According to a sixth aspect of the present invention, there is provided a process for preparing the 2,4-dihydroxyadipic acid derivative (I) comprising reducing the 2-hydroxy-4-oxoadipic acid derivative (II) to obtain the 2,4-dihydroxyadipic acid derivative (IV), reacting the 2,4-dihydroxyadipic acid derivative (IV) with a metal alkoxide and optionally deprotecting the hydroxy group and/or hydrolyzing the ester group.

According to a seventh aspect of the present invention, there is provided a process for preparing a 3,5,6-trihydroxyhexanoate derivative of the formula:

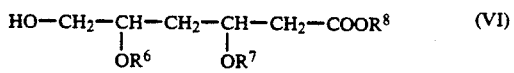  (VI)

wherein $R^6$ and $R^7$ are the same or different and each a hydrogen atom or a protective group of a hydroxy group or together form a ring and $R^8$ is an alkyl group, an aralkyl group or an aryl group, comprising selectively reducing an ester group at the 1-position of a diester of a 2,4-dihydroxyadipate derivative of the formula:

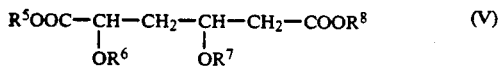  (V)

wherein $R^6$, $R^7$ and $R^8$ are the same as defined above, and $R^5$ is an alkyl group, an aralkyl group or an aryl group.

The processes of the present invention are summarized as follows:

tion of the carboxylic acid group are separately carried out. Then, in a carboxylic acid group at the 4-position of a malic acid derivative prepared by one of the above processes (A), (B) and (C), two carbon atoms are introduced by a conventional method for increasing the number of carbon atoms. For example, the carboxylic acid group is converted to an active ester group with carbonyl diimidazole or a chloroformate, or it is converted to an acid chloride with, for example, thionyl chloride and then the acid chloride is reacted with an agent for increasing the number of carbon atoms by two (e.g. magnesium enolate) to obtain the compound (II) or (III). For example, a protected malic acid derivative which has been prepared by reacting malic acid with 2,2-dimethoxypropane is treated with carbonyl diimidazole (CDI) to form an active ester and then the active ester is treated with a half ester of malonic acid together with magnesium alkoxide or magnesium chloride to obtain the 2-hydroxy-4-oxoadipic acid derivative (II). The above reactions are summarized as follows:

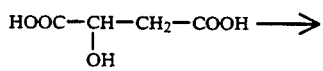

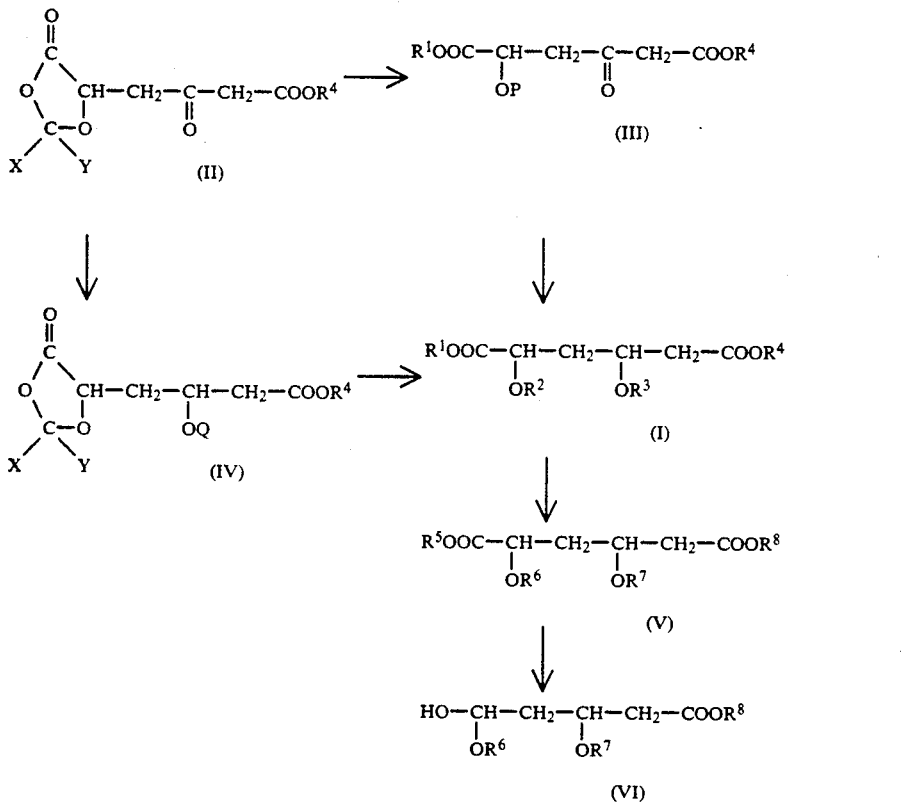

The 2-hydroxy-4-oxoadipic acid derivative (II) or (III) which is used as a starting compound in the present invention is easily prepared from malic acid. For example, in a first process (A), malic acid is reacted with a ketone, an aldehyde or an orthoester to protect both a hydroxy group and a carboxylic acid group at the 1-position (cf. Tetrahedron Letters, 28, 1685 (1987) and 40, 1313 (1984)), in a second process (B), only the carboxylic acid group at the 1-position is esterified (cf. J. Org. Chem., 47, 4931 (1982)), or in a third process (C), the protection of the hydroxy group and the esterifica- -continued

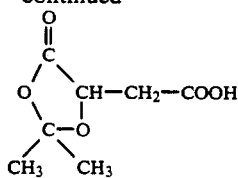

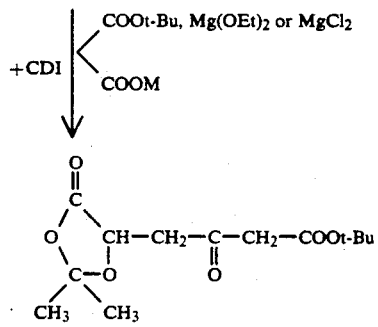

In the present invention, preferably, in the definitions of $R^1$, $R^4$, X and Y, the alkyl group has 1 to 10 carbon atoms, preferably, 1 to 8 carbon atoms, more preferably 1 to 4 carbon atoms, the aralkyl group has 7 to 20 carbon atoms and optionally a substituent such as a nitro group, a halogen atom, a hydroxy group, a $C_1$-$C_{10}$ alkoxy group, etc., and the aryl group has 6 to 20 carbon atoms.

Specific examples of the alkyl group are a methyl group, an ethyl group, a propyl group, an isoproyl group, a butyl group, an isobutyl group, a sec.-butyl group, a tert.-butyl group, a pentyl group, a hexyl group, a heptyl group and an octyl group. Specific examples of the aralkyl group are a benzyl group and a p-nitrobenzyl group. Specific examples of the aryl group are a phenyl group and a tolyl group. Specific examples of the silyl group are a trimethylsilyl group, triethylsilyl group, a triisopropyl group, a tert.-butyldimethylsilyl group, an isobutyldimethylsilyl group, a hexyldimethylsilyl group and a tert.-butyldiphenylsilyl group.

As the protective group $R^2$, $R^3$, P or Q, various protective groups disclosed in Theodor W. Greene, "Protective Group in Organic Synthesis", pages 10–113 (John Wiley & Sons, Inc.) 1981 may be used. Examples are an ester-type protective group (e.g. an acetyl group and a benzoyl group), an ether-type protective group (e.g. a benzyl group and p-nitrobenzyl group), an alkyl group (e.g. trityl group), a silyl-type protective group (e.g. trimethylsilyl, triethylsilyl, triisopropylsilyl, tert.-butyldimethylsilyl, isobutyldimethylsilyl, hexyldimethylsilyl and tert.-butyldiphenylsilyl), a carbonate-type protective group (e.g. tert.-butoxycarbonyl and benzyloxycarbonyl).

When $R^2$ and $R^3$ together form a ring, the ring may be an acetal type protective group of an 1,3-diol in which $R^2$ and $R^3$ together represent isopropylidene, methylene, ethylidene, sec.-butylidene, 1,3-dimethylbutylidene, diphenylmethylene, 1-phenylethylidene, cyclohexylidene or cyclopentylidene, or an orthoester type protective group in which $R^2$ and $R^3$ together represent 1-methoxy-1-ethylidene or α-methoxybenzylidene.

In the both steps for converting the 2-hydroxy-4-oxoadipic acid derivative (II) to the derivative (III) and converting the 2,4-dihydroxyadipic acid derviative (IV) to the derivative (II), with the metal alkoxide, the acetal or ketal group is deprotected and simultaneously esterified to give an α-hydroxyester derivative. In these steps, as the metal alkoxide, any of conventional metal alkoxides such as sodium ethoxide, sodium methoxide, sodium isopropoxide, potassium thoxide and the like may be used. Also a metal alkoxide formed from a combination of a base compound such as a metal hydride or a metal amide and an alcohol may be used.

As a reaction medium, a corresponding alcohol alone may be used, although an aprotic solvent such as THF, toluene, ether or dioxane may be used alone or in combination with the alcohol.

For example, when sodium ethoxide is used as the metal alkoxide, preferably a mixed solvent of ethanol and toluene is used, whereby the hydroxyester derivative can be obtained in a high yield.

A reaction temperature is from a freezing point to a boiling point of the solvent. In view of stability of the starting compound and/or the product, the reaction temperature is preferably not higher than 50° C., more preferably not higher than 30° C.

The reductive conversion of the compound (II) or (III) to the compound (IV) or (I) may be carried out by any of reduction methods which are widely used in the reduction of a ketone to an alcohol or a β-ketoester to a β-hydroxyester. For example, a reducing agent such as a hydride (e.g. sodium boron hydride, zinc boron hydride, lithium boron hydride, diisobutylaluminum hydride, sodium bis(2-methoxyethoxy)aluminum hydride, etc.) is used for reduction. Alternatively, the compound may be catalytically hydrogenated by using a hydrogenation catalyst such as Pd/C, $PtO_2$ or Raney nickel.

By the reduction of the compound (II) or (III), the compound (IV) or (I) having two configurations, namely the syn form and the anti form may be produced, and a ratio of these two forms varies with the reducing method. To selectively prepare the preferable compound having the syn form configuration, a combination of sodium borohydride and trialkylborane, or diisobutylaluminum hydride, zinc borohydride or lithium borohydride can be used. The suitable reduction method is selected according to the kind of the substrate. For example, when the 2-(S)-hydroxy-4-oxoadipic acid derivative which is derived from L-malic acid is reduced as an example of the reduction of the compound (III), it can be reduced with sodium borohydride in the presence of triethylborane at a comparatively low temperature of −70° C. or lower to give (2S,4R)-2,4-dihydroxyadi acid derivative with a high stereoselectivity.

In the reduction product from the compound (II) or (III), the protective group of the hydroxy group such as $R^2$, $R^3$, P or Q may be introduced. For example, to effect the ketal-type protection of an 1,3-diol of the compound (I) in which both $R^2$ and $R^3$ are hydrogen atoms through the formation of an isopropylidene group from $R^2$ and $R^3$, the 1,3-diol (I) is treated with a combination of acetone and sulfuric acid or a combination of dimethoxypropane and pyridinium salt of p-toluenesulfonic acid.

If desired, the ester group can be hydrolyzed. For example, the compound (I) in which $R^1$ is a methyl group and $R^3$ is a tert.-butyl group is treated with an aqueous solution of sodium hydroxide to convert only the $R^3$ group to a carboxyl group.

When the 2,4-dihydroxyadipate derivative (V) is position-selectively reduced with the hydride reducing agent to obtain the 3,5,6-trihydroxyhexanoic acid derivative (VI), $R^5$ may be a lower alkyl group (e.g. methyl group, an ethyl group, a n-propyl group, an isopropyl group or a butyl group) or an aralkyl group (e.g. a benzyl group or a phenethyl group. Among them, a lower alkyl group such as a methyl group or an ethyl group is preferred in view of economy and reduction selectivity. In this case, $R^8$ may be an alkyl group (e.g. a methyl group, an ethyl group, a n-propyl group, an isopropyl group or a tert.-butyl group) or an aralkyl group (e.g. a benzyl group or a phenethyl group). Among them, a tert.-butyl group is preferred in view of the reduction selectivity.

The most preferred combination of the ester groups is the methyl group as $R^5$ and the tert.-butyl group as the $R^8$. As $R^6$ and $R^7$, the hydrogen atom may provide the position selectivity for the reduction, but the ketal type protective group (e.g. an isopropylidene group and a cyclohexylidene group), the acetal type protective group (e.g. a butylidene group and a benzylidene group) or the silyl type protective group (e.g. a tert.-butyldimethylsilyl group and a tert.-butylphenylsilyl group) is preferred since such protective group achieves a higher reduction selectivity.

As the hydride reducing agent, sodium borohydride, lithium aluminum hydride, sodium trimethoxyborohydride, sodium triacetoxyborohydride or sodium diacetoxyborohydride is preferably used. Among them, sodium borohydride is preferred in view of handling properties. An amount of the reducing agent may vary with the kind of the reducing agent. In case of sodium borohydride, 0.5 to 2.5 moles, preferably 1 to 2 moles are used per one mole of the diadipate derivative.

When sodium boron hydride is used, a reaction solvent is a lower alcohol such as methanol, ethanol or isopropanol or an aprotic solvent such as THF, ether or dioxane, or a mixture thereof. Among them, the lower alcohol achieves a high reduction selectivity.

The reaction temperature is from $-50°$ to $+50°$ C., preferably from $-20°$ to $+20°$ C.

PREFERRED EMBODIMENTS OF THE INVENTION

The present invention will be illustrated by following Examples, which will not limit the scope of the present invention.

EXAMPLE 1

Preparation of tert.-butyl 4-(2,2-dimethyl-5-oxo-1,3-dioxolan-4-yl)-3-oxobutanoate To a solution of 2,2,-dimethyl-5-oxo-1,3-dioxolan-4-acetic acid (2.09 g, 12 mmol) in THF (72.0 ml), carbonyldiimidazole (2.14 g, 13.2 mmol) was added in an argon atmosphere at 0° C. and stirred for 15 minutes followed by stirring at room temperature for 4 hours. To the resulting solution, magnesium bis(mono-tert.-butyl malonate) (5.35 g, 15.6 mmol) was added at room temperature and stirred for 18 hours. After evaporating THF off under reduced pressure, a 25 % aqueous solution of citric acid (100 ml) was added, and then the mixture was extracted with ethyl acetate. The organic layer was washed with a saturated aqueous solution of sodium hydrogencarbonate (150 ml), dried over sodium sulfate and concentrated under reduced pressure. The residue was subjected to silica gel column chromatography (hexane: ethyl acetate =3:1) to give pure tert.-butyl 4-(2,2-dimethyl-5 oxo-1,3-dioxolan-4-yl)-3-oxobutanoate (3.14 g, 11.5 mmol). Yield, 96.1 %.

$^1$H-NMR (90 MHz, CDCl$_3$) $\delta$=4.71 (m, 1H), 3.37 (s, 2H), 3.10 (m, 2H), 1.61 (s, 3H), 1.56 (s, 3H), 1.46 (s, 9H).

Elemental analysis (C$_{13}$H$_{20}$O$_6$)

Found: C 57.57 %, H 7.23 %.
Calc'd: C 57.34 %, H 7.40 %.

EXAMPLE 2

Preparation of 1-methyl 6-tert.-butyl 2-hydroxy-4-oxoadipate

To a solution of tert.-butyl 4-(2,2-dimethyl-5-oxo-1,3-dioxolan-4-yl)-3-oxobutanoate (16.30 g, 60.08 mmol) in toluene (120.0 ml) which had been cooled to 0° C., sodium methoxide (1M in methanol) (60.3 ml) was dropwise added in an argon atmosphere. After stirring the solution at 0° C. for 30 minutes, 1N hydrochloric acid (160.5 ml) was dropwise added and the mixture was stirred for 10 minutes at 0° C. Most of the organic solvent was evaporated off under reduced pressure, and the residual mixture was extracted with ethyl acetate and washed with a saturated saline and a phosphate buffer solution (pH 7.0). The organic layers were combined, dried over sodium sulfate and concentrated under reduced pressure. The residue was subjected to silica gel column chromatography (hexane:acetone=2:1) to give pure 1-methyl 6-tert.-butyl 2-hydroxy-4-oxoadipate (13.26 g, 53.85 mmol). Yield, 89.6 %.

$^1$H-NMR (90 MHz, CDCl$_3$) $\delta$=4.52 (m, 1H), 3.95 (br, 2H), 3.80 (s, 3H), 3.40 (s, 2H), 3.04 (m, 2H), 1.46 (s, 9H).

Elemental analysis (C$_{11}$H$_{18}$O$_6$)

Found: C 53.45 %, H 7.27 %.
Calc'd: C 53.65 %, H 7.37 %.

EXAMPLE 3

Preparation of 1-methyl 6-tert.-butyl 2,4 dihydroxyadipate

A mixture of THF (133.05 ml), methanol (66.52 ml) and triethylborane (1M in THF) (72.71 ml) was stirred at room temperature for one hour in an argon atmosphere. To a solution of 1-methyl 6-tert.-butyl 2-hydroxy-4-oxoadipate (12.79 g, 51.94 mmol) in THF (312 ml) cooled to −78° C., the above boran solution was dropwise added over 45 minutes. After stirring the mixture at −78° C. for 50 minutes, sodium borohydride (2.26 g, 59.72 mmol) was added in one portion, followed by stirring at −78° C. for 3 hours. After dropwise adding a mixed solvent of acetic acid and methanol (1:1) (54 ml) to the reaction solution at −78° C. over 15 minutes, the solution was stirred for additional 15 minutes. The resulting mixture was poured in a 5 % solution of ammonium chloride (511 ml) and stirred for 15 minutes. After adjusting pH to 7.5, the organic layer was evaporated off under reduced pressure. After adding 10 % aqueous hydrogen peroxide (104 ml) and adjusting pH of the mixture to 7, a 5 % aqueous solution of sodium sulfite (312 ml) was added, followed by stirring at room temperature for 40 minutes. Then the mixture was extracted with ethyl acetate, and organic layers were colleted, dried over sodium sulfate and concentrated under reduced pressure. The residue was subjected to silica gel column chromatography (hexane:acetone=2:1) to give pure 1-methyl 6-tert.-butyl 2,4-dihydroxyadipate (11.22 g, 45.19 mmol). Yield, 87 %.

$^1$H-NMR (90 MHz, CDCl$_3$) δ=4.33 (m, 2H), 3.76 (s, 3H), 3.61 (br, 2H), 2.42 (m, 2H), 1.97 (m, 2H), 1.46 (s, 9H).

Elemental analysis (C$_{11}$H$_{20}$O$_6$)

Found C 53.37 %, H 8.23 %.
Calc'd: C 53.21 %, H 8.12 %.

EXAMPLE 4

Preparation of 2-methoxycarbonyl-4-tert.-butoxycarbonylmethyl-6,6-dimethyl-1,5-dioxane To a solution of 1-methyl 6-tert.-butyl 2,4-dihydroxyadipate (4.98 g, 20.01 mmol) in methylene chloride (2 dimethoxypropane (9.6 ml, 78 mmol) and pyridinium p-toluenesulfonate (2.01 g, 8 mmol) were added and stirred under reflux conditions for one hour, followed by further stirring at 40° C. for 3 hours while azeotropically removing methanol with methylene chloride. After concentration under reduced pressure, the residue was dissolved in ethyl acetate and poured in water. Then, the mixture was extracted with ethyl acetate. The organic layers were combined, dried over sodium sulfate and concentrated under reduced pressure. The residue was subjected to silica gel column chromatography (hexane:acetone=3:1) to give pure 2-methoxycarbonyl-4-tert.-butoxycarbonylmethyl-6,6-dimethyl-1,5-dioxane (4.89 g, 17.01 mmol). Yield, 85 %.

$^1$H-NMR (90 MHz, CDCl$_3$)δ=4.70–4.17 (m, 2H), 3.76 (s, 3H), 2.41 (m, 2H), 2.13–1.56 (m, 2H), 1.46 (m, 15H).

Elemental analysis (C$_{14}$H$_{24}$O$_6$)

Found: C 58.38 %, H 8.42 %.
Calc'd: C 58.31 %, H 8.39 %.

EXAMPLE 5

Preparation of tert.-butyl 3,5-O-isopropylidene-3,5,6-trihydroxyhexanoate

To a solution of 2-methoxycarbonyl-4-tert.-butoxycarbonylmethyl-6,6-dimethyl-1,5-dioxane (2.88 g, 10 mmol) in methanol (160 ml), sodium boron hydride (1.89 g, 50 mmol) was added in one portion and stirred at room temperature for 12 hours in an argon atmosphere. After evaporating methanol off under reduced pressure, water was added at 0° C. and pH of the mixture was adjusted to 7 with 1N hydrochloric acid. Then, the mixture was extracted with ethyl acetate, and the organic layers were combined, dried over sodium sulfate and concentrated under reduced pressure. The residue was subjected to silica gel column chromatography (hexane: ethyl acetate=3:1) to give pure tert.-butyl 3,5-O-isopropylidene-3,5,6-trihydroxyhexanoate (2.27 g, 8.7 mmol). Yield, 87%.

$^1$H-NMR (90 MHz, CDCl$_3$) δ=4.43–3.82 (m, 2H), 3.68–3.44 (m, 2H), 2.71–2.32 (m, 3H), 1.82–1.5 (m, 2H), 1.47 (s, 9H), 1.45 (d, 6H, J =4 Hz).

Elemental analysis (C$_{13}$H$_{24}$O$_5$)

Found: C 59.97 %, H 9.46 %.
Calc'd: C 59.98 %, H 9.29 %.

EXAMPLE 6

Preparation of tert.-butyl 4-(2-methyl-5-oxo-1,3-dioxolan-4-yl)-3-oxobutanoate

To a solution of 2-methyl-5-oxo-1,3-dioxolan-4-acetic acid (8.01 g, 50 mmol) in THF (300.0 ml), carbonyldiimidazole (8.92 g, 55 mmol) was added at 0° C. in an argon atmosphere and stirred for 15 minutes, followed by further stirring at room temperature for 4 hours. To the resulting solution, magnesium bis(mono-tert.-butyl malonate) (22.27 g, 65 mmol) was added at room temperature and stirred for 40 hours. After evaporating THF off under reduced pressure, a 25% aqueous solution of citric acid was added, and the mixture was extracted with ethyl acetate. The organic layer was washed with a saturated aqueous solution of sodium hydrogencarbonate, dried over sodium sulfate and concentrated under reduced pressure. The residue was subjected to silica gel column chromatography (hexane:ethyl acetate=3:1) to give pure tert.-butyl 4-(2-methyl-5-oxo-1,3-dioxolan-4-yl)-3-oxobutanoate (9.80 g, 38 mmol). Yield, 75.9%.

$^1$H-NMR (90 MHz, CDCl$_3$) δ=5.96–5.53 (m, 1H), 4.67 (m, 1H), 3.40 (s, 2H), 3.13 (m, 2H), 1.56 (d, 3H), 1.46 (s, 9H).

Elemental analysis (C$_{12}$H$_{18}$O$_6$)

Found: C 55.99 %, H 6.95 %.
Calc'd C 55.80 %, H 7.03 %.

EXAMPLE 7

Preparation of tert.-butyl 4-(2-tert.-butyl-5-oxo-1,3-dioxolan-4-yl)-3-oxobutanoate To a solution of 2-tert.-butyl-5-oxo-1,3-dioxolan-4-acetic acid (10.11 g, 50 mmol) in THF (300.0 ml), carbonyldiimidazole (8.92 g, 55 mmol) was added at 0° C. in an argon atmosphere and stirred for 15 minutes, followed by further stirring at room temperature for 4 hours. To the resulting solution, magnesium bis(mono-tert.-butyl malonate) (22.27 g, 65 mmol) was added at room temperature and stirred for 40 hours. After evaporating THF off under reduced pressure, a 25 % aqueous solution of citric acid was added, and the mixture was extracted with ethyl acetate. The organic layer was washed with a saturated aqueous solution of sodium hydrogencarbonate, dried over sodium sulfate and concentrated under reduced pressure. The residue was subjected to silica gel column chromatography (hexane:acetone=3:1) to give pure tert.-butyl 4-(2-tert.-butyl-5-oxo-1,3-dioxolan-4-yl)-3-oxobutanoate (11.51 g, 38 mmol). Yield, 76.6%.

$^1$H-NMR (90 MHz, CDCl$_3$) δ=5.23 (m, 1H), 4.80–4.49 (m, 1H), 3.41 (m, 2H), 3.10 (m, 2H), 1.47 (s, 9H), 0.83 (s, 9H).

Elemental analysis (C$_{15}$H$_{24}$O$_6$)

Found: C 59.76 %, H 8.09 %.
Calc'd: C 59.98 %, H 8.05 %.

EXAMPLE 8

Preparation of 1-methyl 6-tert.-butyl 2-hydroxy-4-oxoadipate

To a solution of 1-methyl malate (920 mg, 6.21 mmol) in THF (40.0 ml), carbonyldiimidazole (1.11 g, 6.8 mmol) was added at 0° C in an argon atmosphere and stirred for 15 minutes, followed by further stirring at room temperature for 4 hours. To the resulting solution, magnesium bis(mono-tert.-butyl malonate) (3.05 g, 8.9 mmol) was added at room temperature and stirred for 40 hours. After evaporating THF off under reduced pressure, a 25 % aqueous solution of citric acid was added, and the mixture was extracted with ethyl acetate. The organic layer was washed with a saturated aqueous solution of sodium hydrogencarbonate, dried over sodium sulfate and concentrated under reduced pressure. The residue was subjected to silica gel column chromatography (hexane:acetone=2:1) to give pure 1-methyl 6-tert.-butyl 2-hydroxy-4-oxoadipate (26.8 mg, 1.1 mmol). Yield, 18 %.

The chemical shifts in $^1$H-NMR analysis were the same as those in Example 2.

EXAMPLE 9

Preparation of tert.-butyl (3R,5S)-3,5-O-isopropylidene-3,5,6-trihydroxyhexanoate In the same manner as in Example 1 but using (4S)-2,2-dimethyl-5-oxo-1,3-dioxolan-4-acetic acid (2.09 g, 12 mmol) derived from L-malic acid as a starting material for the preparation of tert.-butyl 4-(2,2-dimethyl-5-oxo-1,3-dioxolan-4-yl)-3-oxobutanoate, tert.-butyl 4-(2,2-dimethyl-5-oxo-1,3-dioxolan-(4S)-4-yl)-3-oxobutanoate was prepared. Then, by repeating the same procedures of Examples 2-5, tert.-butyl (3R,5S)-3,5-O-isopropylidene-3,5,6-trihydroxyhexanoate was prepared.

The chemical shifts in $^1$H-NMR analysis were the same as those in Example 5.

Elemental analysis ($C_{13}H_{24}O_5$)

Found: C 60.10 %, H 9.21 %.
Calc'd: C 59.98 %, H 9.29 %.
$[\alpha]D$: $-4.06°$ (c=2.1, methanol).

EXAMPLE 10

Preparation of tert.-butyl 3,5-O-isopropylidene-3,5,6-trihydroxyhexanoate

To a solution of 2-methoxycarbonyl-4-tert.-butoxycarbonylmethyl-6,6-dimethyl-1,5-dioxane (2.88 g, 10 mmol) in diethyl ether (40 ml), lithium aluminum hydride (0.38 g, 10 mmol) was added at $-15°$ C. in an argon atmosphere and stirred for 15 hours, followed by stirring at room temperature for 3 hours. After adding methanol at 0° C. and stirring for 30 minutes, pH of the mixture was adjusted to 7 with 1N hydrochloric acid, and the mixture was extracted with ethyl acetate. The organic layers were combined, dried over sodium sulfate and concentrated under reduced pressure. The residue was subjected to silica gel column chromatography (hexane:ethyl acetate=3:2) to give pure tert.-butyl 3,5-O-isopropylidene-3,5,6-trihydroxyhexanoate (2.32 g, 8.9 mmol). Yield, 89 %.

The chemical shifts in $^1$H-NMR analysis were the same as those in Example 5.

EXAMPLE 11

Preparation of tert.-butyl 4-(2,2-dimethyl-5-oxo-1,3-dioxolan-4-yl)-3-hydroxybutanoate To a solution of tert.-butyl 4-(2,2-dimethyl-5-oxo-1,3-dioxolan-4-yl)-3-oxobutanoate (10.88 g, 40.0 mmol) in THF (20 ml), a mixture of THF (96.0 ml) and triethylborane 1M in THF) (56.0 ml) was was added at $-78°$ C. over 45 minutes, followed by stirring at $-78°$ C. for 50 minutes. Thereafter, to the resulting mixture, sodium borohydride (1.51 g, 40.0 mmol) was added in one portion and stirred at $-78°$ C. for 4 hours. After adding 1N hydrochloric acid at 0° C., the mixture was extracted with ethyl acetate and washed with saturated saline. The organic layers were combined, dried over sodium sulfate and concentrated under reduced pressure. The residue was subjected to silica gel column chromatography (hexane:ethyl acetate=2:1) to give pure tert.-butyl 4-(2,2-dimethyl-5-oxo-1,3-dioxolan-4-yl)-3-hydroxybutanoate (6.08 g, 22.16 mmol). Yield, 55%.

$^1$H-NMR (90 MHz, CDCl$_3$) $\delta$=4.71 (m, 1H), 4.28 (br, 1H), 3.40 (m, 1H), 2.50 (m, 2H), 2.00 (m, 2H), 1.61 (s, 1.56 (s, 3H), 1.46 (s, 9H).

Elemental analysis ($C_{13}H_{22}O_6$)

Found: C 57.07 %, H 8.13 %.
Calc'd: C 56.92 %, H 8.08 %.

Preparation of 1-methyl 6-tert.-butyl 2,4-dihydroxyadipate

To a solution of tert.-butyl 4-(2,2-dimethyl-5-oxo-1,3-dioxolan-4-yl)-3-hydroxybutanoate (5.49 g, 20.0 mmol) in toluene (40.0 ml), sodium methoxide (1M in methanol) (30 ml) was added at 0° C. in an argon atmosphere and stirred at 0° C. for 30 minutes. After dropwise adding 1N hydrochloric acid (30.5 ml) at 0° C. over 10 minutes, the mixture was stirred at 0° C. for 10 minutes. After evaporating off the most of the organic solvent under reduced pressure, the residual mixture was extracted with ethyl acetate. The organic layer was washed with a saturated saline and a phosphate buffer (pH 7.0). The organic layers were combined, dried over sodium sulfate and concentrated under reduced pressure. The residue was subjected to silica gel column chromatography (hexane:acetone=2:1) to give pure 1-methyl 6-tert.-butyl 2,4-dihydroxyadipate (3.69 g, 14.9 mmol). Yield, 74.3 %.

The chemical shifts in $^1$H-NMR analysis were the same as those in Example 3.

Elemental analysis ($C_{11}H_{20}O_6$)

Found: C 53.29 %, H 8.10 %.
Calc'd: C 53.21 %, H 8.12 %.

EXAMPLE 13

Preparation of 1-methyl 6-tert.-butyl 2-hydroxy-4-oxoadipate

To a solution of tert.-butyl 4-(2-methyl-5-oxo-1,3-dioxolan-4-yl)-3-oxobutanoate (5.16 g, 20.0 mmol) in toluene (40.0 ml), sodium methoxide (1M in methanol) (20.5 was added at 0° C. over 10 minutes in an argon atmosphere and stirred at 0° C. for 30 minutes. After dropwise adding 1N hydrochloric acid (21.0 ml), the mixture was stirred at 0° C. for 10 minutes. After evaporating off the most of the organic solvent under reduced pressure, the mixture was extracted with ethyl acetate and washed with a saturated saline and a phosphate buffer (pH 7.0). The organic layers were combined, dried over sodium sulfate and concentrated under reduced pressure. The residue was subjected to silica gel column chromatography (hexane:acetone=2:1) to give pure 1-methyl 6-tert.-butyl 2-hydroxy-4-oxoadipate (4.39 g, 17.83 mmol). Yield, 89.2 %.

The chemical shifts in $^1$H-NMR analysis were the same as those in Example 2.

Elemental analysis ($C_{11}H_{18}O_6$)

Found: C 53.59 %, H 7.45 %.
Calc'd: C 53.65 %, H 7.37 %.

EXAMPLE 14

Preparation of 1-ethyl 6-tert.-butyl 2-hydroxy-4-oxoadipate

To a solution of tert.-butyl 4-(2,2-dimethyl-5-oxo-1,3-dioxolan-4-yl)-3-oxobutanoate (16.30 g, 60.08 mmol) in a mixed solvent of toluene (120.0 ml) and ethanol (60.0 ml), sodium methoxide (4.91 g, 79.10 mmol) was dropwise added at 0° C. in an argon atmosphere and stirred for 30 minutes. After dropwise adding 1N hydrochloric acid (80.5 ml), the mixture was stirred at 0° C. for 10 minutes. After evaporating off the most of the organic solvent under reduced pressure, the mixture was extracted with ethyl acetate and washed with a saturated saline and a phosphate buffer (pH 7.0). The organic layers were combined, dried over sodium sulfate and concentrated under reduced pressure. The residue was subjected to silica gel column chromatography (hexane:acetone=2:1) to give pure 1-ethyl 6-tert.-butyl 2-hydroxy-4-oxoadipate (14.02 g, 53.85 mmol). Yield, 89.6%.

$^1$H-NMR (90 MHz, CDCl$_3$) δ=4.52 (m, 1H), 4.30 (q, 2H), 3.43 (s, 2H), 3.20 (m, 2H), 2.96 (br, 1H), 1.46 (s, H), 1.28 (t, 3H).

Elemental analysis ($C_{12}H_{20}O_6$)

Found: C 55.44 %, H 7.70 %.
Calc'd: C 55.37 %, H 7.75 %.

EXAMPLE 15

Preparation of 1-isopropyl 6-tert.-butyl 2-hydroxy-4-oxoadipate

In an argon atmosphere, sodium hydride (60 % in oil) (6.0 g, 150 mmol) was washed with hexane, dried and then mixed with THF (170 ml). To the mixture cooled at 0° C., isopropanol (30 ml) was dropwise added to obtain a yellow solution.

In a solution of tert.-butyl 4-(2,2-dimethyl-5-oxo-1,3-dioxolan-4-yl)-3-oxobutanoate (13.62 g, 50.00 mmol) in toluene (100.0 ml), the above yellow solution was dropwise added and stirred at 0° C. for 30 minutes. After dropwise adding 1N hydrochloric acid (160.0 ml), the mixture was stirred at 0° C. for 10 minutes. After evaporating off the most of the organic solvent under reduced pressure, the mixture was extracted with ethyl acetate and washed with a saturated saline and a phosphate buffer (pH 7.0). The organic layers were combined, dried over sodium sulfate and concentrated under reduced pressure. The residue was subjected to silica gel column chromatography (hexane: acetone=2:1) to give pure 1-isopropyl 6-tert.-butyl 2-hydroxy-4-oxoadipate (11.07 g, 40.35 mmol). Yield, 80.7%.

$^1$H-NMR (90 MHz, CDCl$_3$) δ=5.12 (m, 1H), 4.47 (m, 1H), 3.43 (s, 2H), 3.25 (br, 1H), 3.00 (m, 2H), 1.46 (s, 9H), 1.30 (s, 3H), 1.23 (s, 3H).

Elemental analysis ($C_{13}H_{22}O_6$)

Found: C 56.84 %, H 8.02 %.
Calc'd: C 56.92 %, H 8.08 %.

EXAMPLE 16

Preparation of tert.-butyl (3R,5S)-3,5-O-isopropylidene-3,5,6-trihydroxyhexanoate To a mixture of sodium borohydride (1.11 g, 30 mmol) and THF (28 ml), 1-methyl 6-tert.-butyl (2S,4R)-2,4-O-isopropylidene-2,4-dihydroxyadipate (2.88 g, 10 mmol) was added at room temperature, and to the resulting reaction mixture, methanol (3.6 ml) was gradually added over one hour at room temperature while stirring. After further stirring for one hour, a 5 % aqueous solution of ammonium chloride (30 ml) was gradually added at 5° C. or lower and then 6N hydrochloric acid (5.3 ml) was added to neutralized the mixture. After evaporating methanol off under reduced pressure, the mixture was extracted with methylene chloride twice (each 50 ml). The extracts were combined, dried over anhydrous sodium sulfate and concentrated under reduced pressure. The residual oily material was subjected to silica gel column chromatography (hexane:acetone=5:1) to give pure tert.-butyl (3R,5S)-3,5-O-isopropylidene-3,5,6-trihydroxyhexanoate (2.47 g, 9.5 mmol). Yield, 95%.

$^1$H-NMR (90 MHz, CDCl$_3$) δ=1.43 (s, 3H), 1.46 (s, 3H), 1.47 (s, 9H), 1.5-1.82 (m, 2H), 2.32-2.71 (m, 3H), 3.44-3.68 (m, 2H), 3.82-4.43 (m, 2H).

IR (neat): 2980, 1720, 1365, 1200, 1150 and 1020 cm$^{-1}$.

$[\alpha]_D^{20}$ = −3.87° (c=2.1, methanol).

EXAMPLE 17

Preparation of tert.-butyl (3R,5S)-3,5-O-isopropylidene-3,5,6-trihydroxyhexanoate To a solution of 1-methyl 6-tert.-butyl (2S,4R)-2,4-O-isopropylidene-2,4-dihydroxyadipate (2.88 g, 10 mmol) in methanol (28 ml) which had been cooled to −20° C., sodium borohydride (1.7 g, 45 mmol) was added by portions over 30 minutes while thoroughly stirring, followed by stirring at room temperature for one hour. A 5 % aqueous solution of ammonium chloride (35 ml) was gradually added at 5° C. or lower and then 6N hydrochloric acid (4.3 ml) was added to neutralize the mixture. After evaporating methanol off under reduced pressure, the mixture was extracted with methylene chloride twice (each 50 ml). The extracts were combined, dried over anhydrous sodium sulfate and concentrated under reduced pressure. The residual oily material was subjected to silica gel column chromatography (hexane: acetone=5:1) to give pure tert.-butyl (3R,5S)-3,5-O-isopropylidene-3,5,6-trihydroxyhexanoate (2.42 g, 9.3 mmol). Yield, 93 %.

EXAMPLE 18

Preparation of tert.-butyl 3,5-O-isopropylidene-3,5,6-trihydroxyhexanoate

To a solution of 2-methoxycarbonyl-4-tert. butoxycarbonylmethyl-6,6-dimethyl-1,5-dioxane (2.88 g, 10 mmol) in diethyl ether (40 ml), lithium aluminum hydride (0.38 g, 10 mmol) was added at −15° C. in an argon atmosphere and stirred for 15 hours, followed by stirring at 0° C. for 3 hours. After adding methanol at 0° C. and stirring the mixture for 30 minutes, pH of the mixture was adjusted to 7 with 1N hydrochloric acid. Then, the mixture was extracted with ethyl acetate. The organic layers were combined, dried over anhydrous sodium sulfate and concentrated under reduced pressure. The residue was subjected to silica gel column chromatography (hexane:ethyl acetate=3:2) to give pure tert.-butyl 3,5-O-isopropylidene-3,5,6-trihydroxyhexanoate (2.32 g, 8.9 mmol). Yield, 89 %.

EXAMPLE 19

Preparation of ethyl (3R,5S)-3,5-O-isopropylidene-3,5,6-trihydroxyhexanoate

To a solution of 1-methyl 6-ethyl (2S,4R)-2,4-O-isopropylidene-2,4-dihydroxyadipate (5.2 g) in ethanol (52 ml), sodium borohydride (1.51 g, 40 mmol) was added by portions at 5° C. or lower over 30 minutes, and the mixture was stirred at room temperature for 3 hours. After gradually adding acetic acid (2.3 ml) at 5° C. or lower, water (300 ml) was added, and the mixture was extracted with methylene chloride twice (each 50 ml). The extracts were combined, dried over anhydrous sodium sulfate and concentrated under reduced pressure. The residual oily material was subjected to silica gel column chromatography (hexane: acetone=3:1) to give pure ethyl (3R,5S)-3,5-O-isopropylidene-3,5,6-trihydroxyhexanoate (3.34 g, 1.44 mmol).

$^1$H-NMR (90 MHz, CDCl$_3$) $\delta$=1.27 (t, 3H, J=6 Hz), 1.43 (s, 3H), 1.50 (s, 3H), 2.26–2.76 (m, 2H), 3.15–3.88 (m, 3H), 3.90–4.58 (m, 4H).

IR (neat): 3475, 2970, 1740, 1380, 1170 and 1020 cm$^{-1}$.

EXAMPLE 20

Preparation of ethyl 4 (2,2-dimethyl-5-oxo-1,3-dioxolan-4-yl)-3-oxobutanoate

To a solution of 2,2-dimethyl-5-oxo-1,3-dioxolan-4-acetic acid (525 mg, 3.01 mmol) in THF (17.0 ml), carbonyldiimidazole (534 mg, 3.29 mmol) was added at 0° C. in an argon atmosphere and stirred for 30 minutes. To the resulting solution, magnesium bis(mono-ethyl malonate) (1.12 g, 3.91 mmol) was added at room temperature and stirred for 23 hours. After evaporating THF off under reduced pressure, a 25 % aqueous solution of citric acid (20 ml) was added, and the mixture was extracted with ethyl acetate. The organic layer was washed with a saturated aqueous solution of sodium hydrogencarbonate (20 ml), dried over sodium sulfate and concentrated under reduced pressure. The residue was subjected to silica gel column chromatography (hexane:ethyl acetate=5:1) to give pure ethyl 4-(2,2-dimethyl-5-oxo-1,3-dioxolan-4-yl)-3-oxobutanoate (506 mg, 2.07 mmol). Yield, 69%.

$^1$H-NMR (90 MHz, CDCl$_3$) $\delta$=4.77 (m, 1H), 4.22 (q, 2H, J =7.5 Hz), 3.50 (s, 2H), 3.10 (m, 2H), 1.62 (s, 3H), 1.57 (s, 3H), 1.28 (t, 3H, J =7.5 Hz).

Elemental analysis (C$_{11}$H$_{16}$O$_6$)

Found: C 54.20 %, H 6.58 %.
Calc'd: C 54.09 %, H 6.60 %.

EXAMPLE 21

Preparation of 1-methyl 6-ethyl 2-hydroxy-4-oxoadipate

To a solution of ethyl 4-(2,2-dimethyl-5-oxo-1,3-dioxolan-4-yl)-3-oxobutanoate (480 mg, 1.97 mmol) in toluene (2.0 ml), sodium methoxide (1M in methanol) (2.1 ml) was dropwise added at 0° C. in an argon atmosphere and stirred for 30 minutes. To the mixture, 1N hydrochloric acid (2.1 ml) was dropwise added and the mixture was stirred at room temperature for 15 minutes. After evaporating off the most of the organic solvent under reduced pressure, the mixture was extracted with ethyl acetate and washed with a saturated saline and a phosphate buffer (pH 7.0). The organic layers were combined, dried over sodium sulfate and concentrated under reduced pressure. The residue was subjected to silica gel column chromatography (hexane:ethyl acetate=5:1) to give pure 1-methyl 6-ethyl 2-hydroxy-4-oxoadipate (366 mg, 1.67 mmol). Yield, 85 %.

$^1$H-NMR (90 MHz, CDCl$_3$) $\delta$=4.52 (m, 1H), 4.18 (q, 2H, J =7.5 Hz), 3.80 (s, 3H), 3.48 (s, 2H), 3.2 (br, 1H), 3.1 (m, 2H), 1.28 (t, 3H, J=7.5 Hz).

Elemental analysis (C$_9$H$_{14}$O$_6$)

Found: C 49.45 %, H 6.35 %.
Calc'd: C 49.54 %, H 6.47 %.

Preparation of 1-methyl 6-ethyl 2,4-dihydroxyadipate

A mixture of THF (2.5 ml), methanol (5 ml) and triethylborane (1M in THF) (12 ml) was stirred at a temperature from −50 to −60° C. for one hour in an argon atmosphere. A solution of 1-methyl 6-ethyl 2-hydroxy-4-oxoadipate (2.2 g, 10 mmol) in THF (2.5 ml) was dropwise added to the above borane solution at −60° C. After stirring at −78° C. for 60 minutes, sodium borohydride (378 mg, 10 mmol) was added in one portion, followed by stirring at −78° C. for 2 hours. After dropwise adding acetic acid (3 ml) to the reaction solution at −78° C., the solution was stirred for 15 minutes. After adding water (5 ml), THF was evaporated off. After adding ethanol (10 ml) and a 10 % hydrogen peroxide (1.5 ml) at room temperature, 1N hydrochloric acid was added to adjust pH to 7, followed by stirring for one hour. After adding a 5 % aqueous solution of sodium sulfite (15 ml) and stirring the mixture at room temperature for 40 minutes, the mixture was extracted with methylene chloride and organic layers were combined, dried over sodium sulfate and concentrated under reduced pressure. The residue was subjected to silica gel column chromatography (hexane:acetone=5:1) to give pure 1-methyl 6-ethyl 2,4-dihydroxyadipate (1.52 g, 6.9 mmol). Yield, 69 %.

$^1$H-NMR (90 MHz, CDCl$_3$) $\delta$=1.26 (t, 3H, J=6 Hz), 1.6–2.2 (m, 2H), 2.51 (d, 2H, J=6 Hz), 3.25–3.6 (br, 2H), 3.78 (s, 3H), 4.16 (q, 2H, J =6 Hz).

Elemental analysis (C$_9$H$_{16}$O$_6$)

Found: C 49.25 %, H 7.11 %.
Calc'd: C 49.09 %, H 7.32 %.

EXAMPLE 23

Preparation of 2-methoxycarbonyl-4-ethoxycarbonylmethyl-6,6-dimethyl-1,5-dioxane To a solution of 1-methyl 6-ethyl 2,4-dihydroxyadipate (1.5 g, 6.81 mmol) in methylene chloride (60 ml), dimethoxypropane (1.672 ml, 78 mmol) and pyridinium p-toluenesulfonate (251 mg, 1 mmol) were added and stirred under reflux conditions for one hour, followed by further stirring at 50° C. for one hour while azeotropically removing methanol with methylene chloride. Then, after adding methylene chloride (60 ml), the mixture was again stirred at 50° C. for one hour to remove methylene chloride (50 ml). To the residue, water was added, and the mixture was extracted with methylene chloride. The organic layers were combined, dried over sodium sulfate and concentrated under reduced pressure. The residue was subjected to silica gel column chromatography (hexane:acetone=5:1) to give pure 2-methoxycarbonyl-4-ethoxycarbonylmethyl-6,6-dimethyl-1,5-dioxane (1.29 g, 4.99 mmol). Yield, 73 %.

$^1$H-NMR (90 MHz, CDCl$_3$) δ=1.28 (t, 6H, J =6 Hz), 1.51 (m, 6H), 1.70–2.1 (m, 2H), 2.45–2.60 (m, 2H), 3.76 (s, 3H), 4.16 (d, 2H, J =6 Hz), 4.2–4.73 (m, 2H).

Elemental analysis (C$_{12}$H$_{20}$O$_6$)

Found: C 55.59 %, H 7.52 %.
Calc'd: C 55.37 %, H 7.74 %.

EXAMPLE 24

Preparation of ethyl 3,5-O-isopropylidene-3,5,6-trihydroxyhexanoate

To a solution of 2-methoxycarbonyl-4-ethoxycarbonylmethyl-6,6-dimethyl-1,5-dioxane (520 mg, 2 mmol) in ethanol (5.2 ml), sodium borohydride (75 mg, 2 mmol) was added by portions on an ice bath and stirred at room temperature for 12 hours in an argon atmosphere. After adding acetic acid (230 μl) on the ice bath and stirring for 30 minutes, water (30 ml) was added, and the mixture was extracted with methylene chloride twice (each 50 ml). The organic layers were combined, dried over sodium sulfate and concentrated under reduced pressure. The residue was subjected to silica gel column chromatography (hexane: ethyl acetate=3:1) to give pure ethyl 3,5-O-isopropylidene-3,5,6-trihydroxyhexanoate (261 mg, 1.12 mmol). Yield, 56%.

$^1$H-NMR (90 MHz, CDCl$_3$) δ=1.26 (t, 3H, J=6 Hz), 1.43 (s, 3H), 1.53 (s, 3H), 1.56–2.0 (m, 2H), 2.43–2.65 (m, 2H), 3.16–3.93 (m, 3H), 3.82–4.63 (m, 4H).

Elemental analysis (C$_{11}$H$_{20}$O$_5$)

Found: C 57.05 %, H 8.59 %.
Calc'd: C 56.88 %, H 8.68 %.

EXAMPLE 25

Preparation of 1-ethyl 6-tert.-butyl 2,4-dihydroxyadipate

A mixture of THF (2.2 ml), methanol (4.4 ml) and triethylborane (1M in THF) (8.52 ml) was stirred at room temperature for one hour in an argon atmosphere. A solution of 1-ethyl 6-tert.-butyl 2-hydroxy-4-oxoadipate (1.85 g, 7.1 mmol) in THF (2 ml) was dropwise added to the above boran solution at room temperature. After stirring at room temperature for 2 hours and cooling the mixture to −78° C., sodium borohydride (229 mg, 6.1 mmol) was added in one portion, followed by stirring at −78° C. for 2 hours. After dropwise adding acetyl chloride (0.26 ml) to the reaction solution at −78° C., the solution was stirred for additional 30 minutes at room temperature. After evaporating methanol off under reduced pressure, methanol (30 ml) was added to the mixture and again methanol was evaporated off under reduced pressure. After adding methylene chloride (20 ml) and water (20 ml), pH of the mixture was adjusted to 6 with 1N hydrochloric acid, and mixture was separated. The aqueous layer was extracted with methylene chloride twice (each 50 ml), and organic layers were combined and washed with water (30 ml). After drying the organic solution over anhydrous sodium sulfate, the solvent was concentrated under reduced pressure. The residue was subjected to silica gel column chromatography (hexane:acetone=5:1) to give pure 1-ethyl 6-tert.-butyl 2,4-dihydroxyadipate (1.76 g, 6.73 mmol). Yield, 95 %.

$^1$H-NMR (90 MHz, CDCl$_3$) δ=1.30 (t, 3H, J=6 Hz), 1.46 (s, 9H), 1.88–1.99 (m, 2H), 2.43 (d, 2H, J=6

Elemental analysis (C$_{12}$H$_{22}$O$_6$)

Found: C 54.80 %, H 8.26 %.
Calc'd: C 54.94 %, H 8.45 %.

EXAMPLE 26

Preparation of 2-ethoxycarbonyl-4-tert.-butoxycarbonylmethyl-6,6-dimethyl-1,5-dioxane To a solution of 1-ethyl 6-tert.-butyl 2,4-dihydroxyadipate (1.6 g, 6.1 mmol) in methylene chloride (60 ml), dimethoxypropane (1.672 ml, 78 mmol) and pyridinium p-toluenesulfonate (251 mg, 1 mmol) were added and stirred under reflux conditions for one hour, followed by further stirring at 50° C for one hour while azeotropically removing methanol with methylene chloride. To the mixture, methylene chloride (60 ml) was added and stirred at 50° C. for one hour to remove methylene chloride. After adding water, the mixture was extracted with methylene chloride. The organic layers were combined, dried over sodium sulfate and concentrated under reduced pressure. The residue was subjected to silica gel column chromatography (hexane:acetone=7:1) to give pure 2-ethoxycarbonyl-4-tert.-butoxycarbonylmethyl-6,6-dimethyl-1,5-dioxane (1.23 g, 4.06 mmol). Yield, 67%.

$^1$H-NMR (90 MHz, CDCl$_3$) δ=1.28 (t, 3H, J=6 Hz), 1.43–1.50 (m, 19H), 1.92 (m, 1H), 2.31–2.48 (m, 2H), 4.21 (q, 2H, J=6 Hz), 4.32 (m, 1H), 4.51 (m, 1H).

Elemental analysis (C$_{15}$H$_{26}$O$_6$)

Found: C 59.33 %, H 8.85 %.
Calc'd: C 59.58 %, H 8.67 %.

EXAMPLE 27

Preparation of tert.-butyl 3,5-O-isopropylidene-3,5,6-trihydroxyhexanoate

To a suspension of sodium borohydride (170 mg, 4.5 mmol) in THF (3 ml), a solution of 2-ethoxycarbonyl-4-tert.-butoxycarbonylmethyl-6,6-dimethyl-1,5-dioxane (605 mg, 2 mmol) in ethanol (2.1 ml) was added by portions at room temperature, followed by stirring at room temperature for 4 hours. To the mixture cooled on an ice bath, acetic acid (260 μl) was added and the mixture was stirred for 30 minutes. After adding water (30 ml), the mixture was extracted with methylene chloride twice (each 50 ml), and the organic layers were combined, dried over sodium sulfate and concentrated under reduced pressure. The residue was subjected to silica gel column chromatography (hexane: ethyl acetate=5:1) to obtain pure tert.-butyl 3,5-O-isopropylidene-3,5,6-trihydroxyhexanoate (494 mg, 1.89 mmol). Yield, 95 %.

The chemical shifts in $^1$H-NMR analysis were the same as those in Example 5.

What is claimed is:

1. A 2,4-dihydroxyadipic acid derivative of the formula:

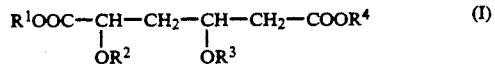

wherein $R^1$ and $R^4$ are the same or different and each a hydrogen atom, an alkyl group, an aralkyl group, an aryl group or a silyl group, and $R^2$ and $R^3$ are the same or different and each a hydrogen atom or a protective group of a hydroxy group or together form a ring.

2. A 2-hydroxy-4-oxoadipic acid derivative of the formula:

$$R^1OOC-CH-CH_2-\underset{\underset{O}{\|}}{C}-CH_2-COOR^4 \qquad \text{(III)}$$
$$\phantom{R^1OOC-C}OP$$

wherein $R^1$ and $R^4$ are the same or different and each a hydrogen atom, an alkyl group, an aralkyl group, an aryl group or a silyl group, and P is an hydrogen atom or a protective group of a hydroxy group.

3. The compound according to any one of claims 1 or 3, wherein $R^4$ is a tert.-butyl group.

4. The compound according to claim 1 or 2, wherein $R^1$ is a $C_1$–$C_4$ alkyl group.

5. The compound according to claim 1, wherein $R^2$ and $R^3$ are both hydrogen atoms.

6. The compound according to claim 1, wherein $R^2$ and $R^3$ together form an isopropylidene group.

7. The compound according to claim 1, wherein $R^1$ is a $C_1$–$C_4$ alkyl group, $R^2$ and $R^3$ are both hydrogen atoms, and $R^4$ is a tert.-butyl group.

8. The compound according to claim 1, wherein $R^1$ is a methyl group or an ethyl group, $R^2$ and $R^3$ are both hydrogen atoms, and $R^4$ is a tert.-butyl group.

9. The compound according to claim 1, wherein $R^1$ is a $C_1$–$C_4$ alkyl group, $R^2$ and $R^3$ together form an isopropylidene group, and $R^4$ is a tert.-butyl group.

10. The compound according to claim 2, wherein P is a hydrogen atom.

11. The compound according to claim 2, wherein $R^1$ is a $C_1$–$C_4$ alkyl group, P is a hydrogen atom, and $R^4$ is a tert.-butyl group.

12. The compound according to claim 2, wherein $R^1$ is a methyl group or an ethyl group, P is a hydrogen atom, and $R^4$ is a tert.-butyl group.

13. A process for preparing a 3,5,6-trihydroxyhexanoate derivative of the formula:

$$HO-CH_2-CH-CH_2-CH-CH_2-COOR^8 \qquad \text{(VI)}$$
$$\phantom{HO-CH_2-C}OR^6 \phantom{-CH_2-}OR^7$$

wherein $R^6$ and $R^7$ are the same or different and each a hydrogen atom or a protective group of a hydroxy group or together form a ring and $R^8$ is an alkyl group, an aralkyl group or an aryl group, comprising selectively reducing an ester group at the 1-position of a diester of a 2,4-dihydroxyadipate derivative of the formula:

$$R^5OOC-CH-CH_2-CH-CH_2-COOR^8 \qquad \text{(V)}$$
$$\phantom{R^5OOC-C}OR^6 \phantom{-CH_2-}OR^7$$

wherein $R^6$, $R^7$ and $R^8$ are the same as defined above, and $R^5$ is an alkyl, group an aralkyl group or an aryl group.

14. The process according to claim 13, wherein $R^6$ and $R^7$ in the formula (V) together form a ketal type or acetal type protective group.

15. The process according to claim 14, wherein $R^6$ and $R^7$ in the formula (V) together form an isopropylidene group.

16. The process according to claim 13, 24 or 25, wherein $R^5$ in the formula (V) is a $C_1$–$C_4$ primary or secondary alkyl group, and $R^8$ is a tert.-butyl group.

17. The process according to claim 13, wherein said 2,4-dihydroxyadipic acid derivative (V) is reduced with a hydride reducing agent.

18. The process according to claim 17, wherein said hydride reducing agent is sodium borohydride.

19. The process according to claim 17, wherein said hydride reducing agent is lithium aluminum hydride.

20. The process according to claim 13, wherein, in the formula(V), $R^5$ is a methyl group or an ethyl group, $R^8$ is a tert.-butyl group, and $R^6$ and $R^7$ together form an isopropylidene group.

* * * * *